(12) United States Patent
Onishi et al.

(10) Patent No.: US 7,148,479 B2
(45) Date of Patent: Dec. 12, 2006

(54) DEFECT INSPECTION APPARATUS, PROGRAM, AND MANUFACTURING METHOD OF SEMICONDUCTOR DEVICE

(75) Inventors: Atsushi Onishi, Kanagawa (JP); Yuichiro Yamazaki, Tokyo (JP); Ichirota Nagahama, Ibaraki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 35 days.

(21) Appl. No.: 11/086,212

(22) Filed: Mar. 23, 2005

(65) Prior Publication Data

US 2005/0230618 A1    Oct. 20, 2005

(30) Foreign Application Priority Data

Mar. 23, 2004    (JP)    ............................ 2004-085545

(51) Int. Cl.
  *H01J 37/256*    (2006.01)
(52) U.S. Cl. ....................... 250/310; 250/398
(58) Field of Classification Search ................ 250/310, 250/398
  See application file for complete search history.

(56) References Cited

U.S. PATENT DOCUMENTS 5,576,833 A      11/1996 Miyoshi et al.
6,855,929 B1 *   2/2005 Kimba et al. ................ 250/310

FOREIGN PATENT DOCUMENTS

JP    04-242060    8/1992
JP    7-249393     9/1995
JP    11-132975    5/1999

\* cited by examiner

Primary Examiner—Kiet T. Nguyen
(74) Attorney, Agent, or Firm—Finnegan, Henderson, Farabow, Garrett & Dunner, L.L.P.

(57) ABSTRACT

A defect inspection apparatus includes a charged particle beam source which emits a charged particle beam to illuminate the charged particle beam onto a sample as a primary beam; an image pickup which includes an imaging element having a light receiving face receiving at least one of a secondary charged particle, a reflective charged particle, and a back-scattered charged particle generated from the sample by the illumination of the primary beam and which outputs a signal indicating a state of the surface of the sample; a mapping projection system which maps/projects at least one of the secondary charged particle, the reflective charged particle, and the back-scattered charged particle as a secondary beam and which makes the beam to form an image on the light receiving face of the imaging element; a controller which adjusts a beam diameter of the primary beam in such a manner as to apply the beam to the sample with a size smaller than that of an imaging region as a target of review to scan the imaging region and which allows the image pickup to pick up a plurality of frame images; an image processor which processes the plurality of obtained frame images to prepare a review image; and a defect judgment unit which judges a defect of the sample based on the review image.

5 Claims, 10 Drawing Sheets

DEFECT INSPECTION APPARATUS, PROGRAM, AND MANUFACTURING METHOD OF SEMICONDUCTOR DEVICE

CROSS REFERENCE TO RELATED APPLICATION

This application claims benefit of priority under 35USC § 119 to Japanese Patent Application No. 2004-085545, filed on Mar. 23, 2004, the contents of which are incorporated by reference herein.

BACKGROUND OF THE INVENTION

1. Field of the Invention

The present invention relates to a defect inspection apparatus, a program, and a manufacturing method of a semiconductor device.

2. Related Background Art

A method has been proposed in which a rectangular electron beam is applied to a sample, a secondary electron, a reflective electron, and a back-scattered electron generated in accordance with a variation of a shape/material/potential of a sample surface are enlarged/projected to acquire a sample surface image, and the image is applied to defect inspection of a semiconductor pattern (e.g., Japanese Patent Laid-Open (kokai) Nos. 07-249393 and 11-132975).

A schematic procedure of a general defect inspection method using a mapping projection type electron beam defect inspection apparatus according to a conventional technique is described. First, after setting parameters such as inspection sensitivity and electron beam condition, inspection is executed, a place extracted as a defect is reviewed in order to confirm an inspection result or optimize sensitivity. At a reviewing time, a magnification is preferably set to be higher than that at an inspection time, and imaging is performed in order to judge whether a defect is true or false. Therefore, inspection sensitivity is checked. When the sensitivity is satisfactory, the inspection is ended. However, when the sensitivity is insufficient, a parameter value is set again, and the above-described procedure is repeated until sufficient sensitivity is obtained.

However, since the mapping projection type electron beam defect inspection apparatus is originally designed in such a manner as to be optimum for the magnification at an inspection time, the apparatus is not suitable for imaging with a high magnification and resolution. Therefore, for example, to cover both the magnifications at an inspection time and at a reviewing time by a single beam lens column, there is a problem that the apparatus becomes huge. Additionally, there is also a method of separately installing a beam lens column for reviewing, but the method is not so preferable.

Additionally, for example, a control electrode is disposed right above a wafer which is a sample, or a stage for supporting the wafer is set to be movable in a Z-direction, and accordingly a working distance between the wafer and an objective lens is narrowed. Consequently, it is also possible to enhance an observation magnification without setting the apparatus to be huge.

However, a sufficient resolution or S/N cannot be obtained in this method.

BRIEF SUMMARY OF THE INVENTION

According to a first aspect of the present invention, there is provided a defect inspection apparatus comprising:

a charged particle beam source which emits a charged particle beam to illuminate the charged particle beam onto a sample as a primary beam, the sample generating a secondary charged particle, a reflective charged particle, and/or a back-scattered charged particle from the surface thereof by the illumination of the primary beam;

an image pickup which includes an imaging element having a light receiving face receiving at least one of the secondary charged particle, the reflective charged particle, and the back-scattered charged particle generated from the sample and which outputs a signal indicating a state of the surface of the sample;

a mapping projection system which maps/projects at least one of the secondary charged particle, the reflective charged particle, and the back-scattered charged particle as a secondary beam and which makes the beam to form an image on the light receiving face of the imaging element;

a controller which adjusts a beam diameter of the primary beam in such a manner as to apply the beam to the sample with a size smaller than that of an imaging region as a target of review to scan the imaging region and which allows the image pickup to pick up a plurality of frame images;

an image processor which processes the plurality of obtained frame images to prepare a review image; and a defect judgment unit which judges a defect of the sample based on the review image.

According to a second aspect of the present invention, there is provided a program which allows a computer connectable to a defect inspection apparatus to execute a defect inspection method, the defect inspection apparatus comprising: a charged particle beam source which emits a charged particle beam to illuminate the charged particle beam as a primary beam onto a sample, the sample generating a secondary charged particle, a reflective charged particle, and/or a back-scattered charged particle from the surface thereof by the illumination of the primary beam; an image pickup which includes an imaging element with a light receiving face to receive at least one of the secondary charged particle, the reflective charged particle, and the back-scattered charged particle generated from the sample and which outputs a signal indicating a state of the surface of the sample; and a mapping projection system which maps/projects at least one of the secondary charged particle, the reflective charged particle, and the back-scattered charged particle as a secondary beam and which makes the beam to form an image on the light receiving face of the imaging element, the defect inspection method comprising:

scanning a sample with the primary beam to acquire a surface image of the sample, and extracting a defect portion from the surface image;

defining a surface region of the sample including the extracted defect portion as an imaging region of a review object, dividing the imaging region into a plurality of frame regions, adjusting a beam diameter of the primary beam in accordance with a size of each frame, and scanning the imaging region with the primary beam having the adjusted beam diameter to acquire a plurality of frame images;

processing the plurality of obtained frame images to prepare a review image; and judging a defect of the sample based on the review image.

According to a third aspect of the present invention, there is provided a manufacturing method of a semiconductor device comprising a defect inspection method using a defect inspection apparatus comprising: a charged particle beam source which emits a charged particle beam to illuminate the charged particle beam as a primary beam onto a sample, the sample generating a secondary charged particle, a reflective charged particle, and/or a back-scattered charged particle from the surface thereof by the illumination of the primary beam; an image pickup which includes an imaging element with a light receiving face to receive at least one of the secondary charged particle, the reflective charged particle, and the back-scattered charged particle generated from the sample and which outputs a signal indicating a state of the surface of the sample; and a mapping projection system which maps/projects at least one of the secondary charged particle, the reflective charged particle, and the back-scattered charged particle as a secondary beam and which makes the beam to form an image on the light receiving face of the imaging element, the defect inspection method comprising:

scanning a sample with the primary beam to acquire a surface image of the sample, and extracting a defect portion from the surface image;

defining a surface region of the sample including the extracted defect portion as an imaging region of a review object, dividing the imaging region into a plurality of frame regions, adjusting a beam diameter of the primary beam in accordance with a size of each frame, and scanning the imaging region with the primary beam having the adjusted beam diameter to acquire a plurality of frame images;

processing the plurality of obtained frame images to prepare a review image; and judging a defect of the sample based on the review image.

DETAILED DESCRIPTION OF THE INVENTION

Embodiments of the present invention will be described hereinafter with reference to the drawings. It is to be noted that in the drawings, the same parts are denoted with the same reference numerals, and redundant description will be performed only when necessary.

FIRST EMBODIMENT

Figure 1:
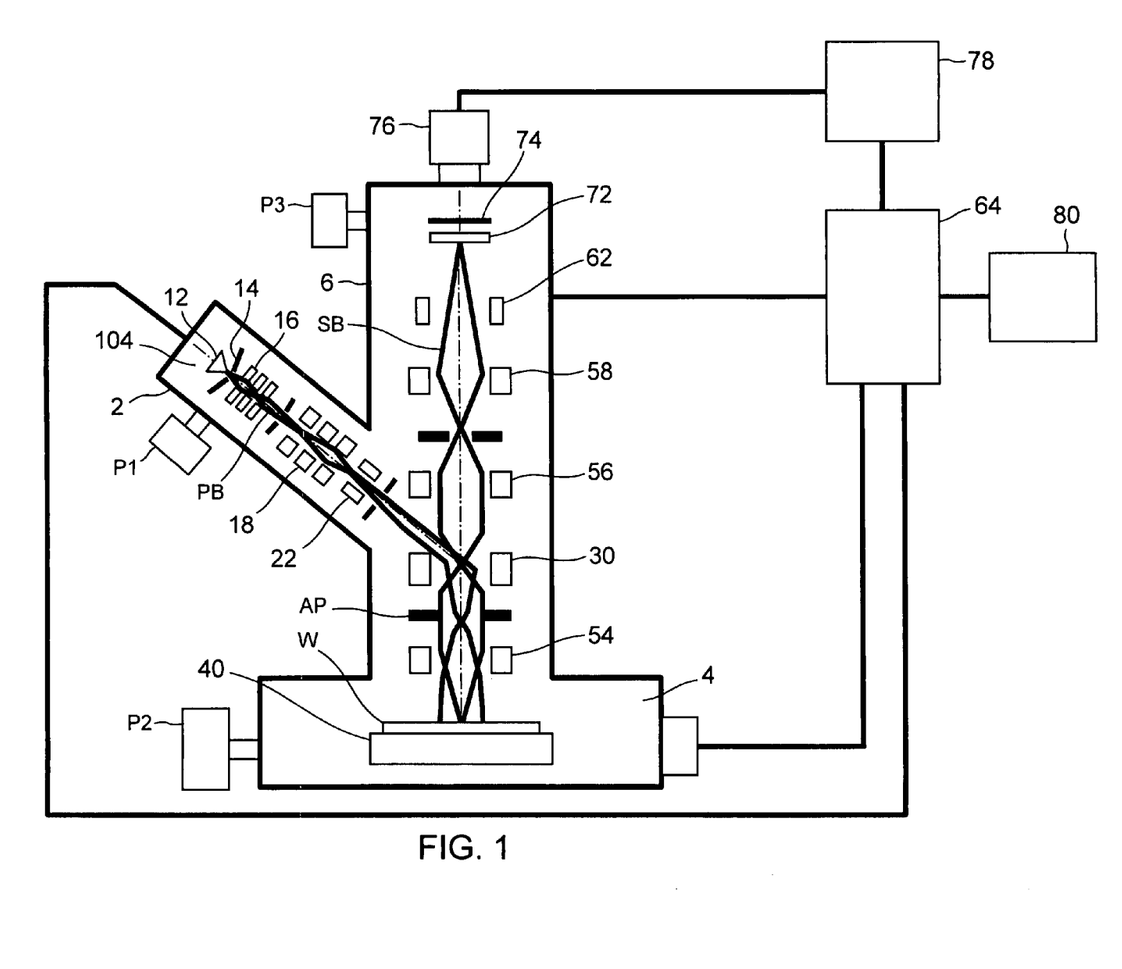
FIG. 1 is a block diagram showing a schematic constitution of one embodiment of a defect inspection apparatus according to the present invention.

FIG. 1 is a block diagram showing a schematic constitution of one embodiment of a defect inspection apparatus according to the present invention. The defect inspection apparatus shown in FIG. 1 comprises a primary column 2, a stage chamber 4, a secondary column 6, a time delay integrator (TDI) sensor 76, a controller 64, a host computer 80, and vacuum pumps P1 to P3.

The host computer 80 corresponds, for example, to a defect judgment unit, controls the whole apparatus including the controller 64, and judges whether a defect obtained by tentative inspection is a true defect or a false defect based on a review image obtained by a defect inspection method described later. The controller 64 corresponds to, for example, a controller, and generates various control signals. The controller supplies the signals to an image processor 78, additionally an electron gun, a quadrupole lens 18, a primary beam deflector 22, an objective lens 54, a Wien filter 30, first and second projection lenses 56, 58, and a secondary beam deflector 62, and controls these components.

The stage chamber 4 contains a stage 40 for supporting a wafer W on which a pattern that is an inspection object is formed on the upper surface. The stage 40 is constituted to be movable in three X-Y-Z directions by the control signal from the controller 64. A vacuum pump P2 is connected to the stage chamber 4, and the inside of the pump is brought into a high vacuum state. The stage 40 is connected to a power supply (not shown), and has a structure in which voltage is applicable to the wafer W.

The primary column 2 includes the electron gun, quadrupole lens 18, and primary beam deflector 22. The electron gun, quadrupole lens 18, and primary beam deflector 22 correspond to, for example, a charged particle beam source. The electron gun has a cathode 12 which emits electrons, a Weh-nelt cylinder 14 having a rectangular opening, and a deflector 16 for adjusting a beam axis. An acceleration voltage, emission current and optical axis of the electron gun are controlled while a primary beam PB is emitted. The primary column 2 is inclined/disposed with respect to a vertical direction of a wafer W surface. By this constitution, the primary beam PB enters the Wien filter 30 from an oblique direction with respect to the surface of the wafer W. The Wien filter 30 is one of electromagnetic field superimposition type deflectors. The filter-deflects the primary beam PB which obliquely enters the filter through the primary column 2 in a vertical direction with respect to a sample face of the wafer W so that the beam enters the wafer W.

The secondary column 6 contains a secondary beam mapping projection system, a micro channel plate (MCP) detector 72, and a fluorescence face 74. The secondary beam mapping projection system corresponds to, for example, a mapping projection system, and includes the objective lens 54, an aperture AP, the Wien filter 30, the first and second projection lenses 56, 58 constituted by, for example, rotationally symmetric electrostatic lenses, and the secondary beam deflector 62. The secondary beam mapping projection system receives the primary beam PB, and guides the secondary electron, reflective electron, and back-scattered electron generated from the surface of the wafer W into the secondary column 6 from the stage chamber 4 by a magnetic field, an electric field, or a combination of the fields. While the electrons are accelerated, they are enlarged/projected and applied as secondary beams into the MCP detector 72. It is to be noted that the Wien filter 30 is controlled with respect to a secondary beam SB applied from a wafer W side on a condition that the beam travels straight. The secondary beam SB travels straight through the Wien filter 30, and is enlarged/projected by the first and second projection lenses 56, 58. The secondary beam deflector 72 deflects the secondary beam SB in such a manner that an incidence face of the MCP detector 72 is scanned by the secondary beam SB in synchronization with the TDI sensor 76.

An electron beam detector corresponds to, for example, an imaging unit, and includes the MCP detector 72, fluorescence face 74, and TDI sensor 76. The secondary beam SB which has entered the MCP detector 72 is amplified into fourth to fifth power times an electron amount on the incidence face by the MCP detector 72 and then applied to the fluorescence face 74. Accordingly, a fluorescence image generated by the fluorescence face 74 is detected by the TDI sensor 76, and supplied to the image processor 78. In the present embodiment, the TDI sensor 76 has a STILL mode. The STILL mode refers to a mode in which a timing signal of the TDI sensor is controlled, and accordingly an image is picked up by a general CCD sensor. The imaging by a frame unit is possible using the STILL mode.

The image processor 78 corresponds to, for example, an image processor which processes a detected signal of a fluorescence image, and supplies the signal as an image signal of an SEM image indicating a state of the surface of the wafer W to the host computer 80 via the controller 64. The image processor 78 is capable of synthesizing an image picked up by a frame unit by an addition process as described later.

Next, several defect inspection methods using the defect inspection apparatus shown in FIG. 1 will be described with reference to FIGS. 2 to 5.

Figure 2:
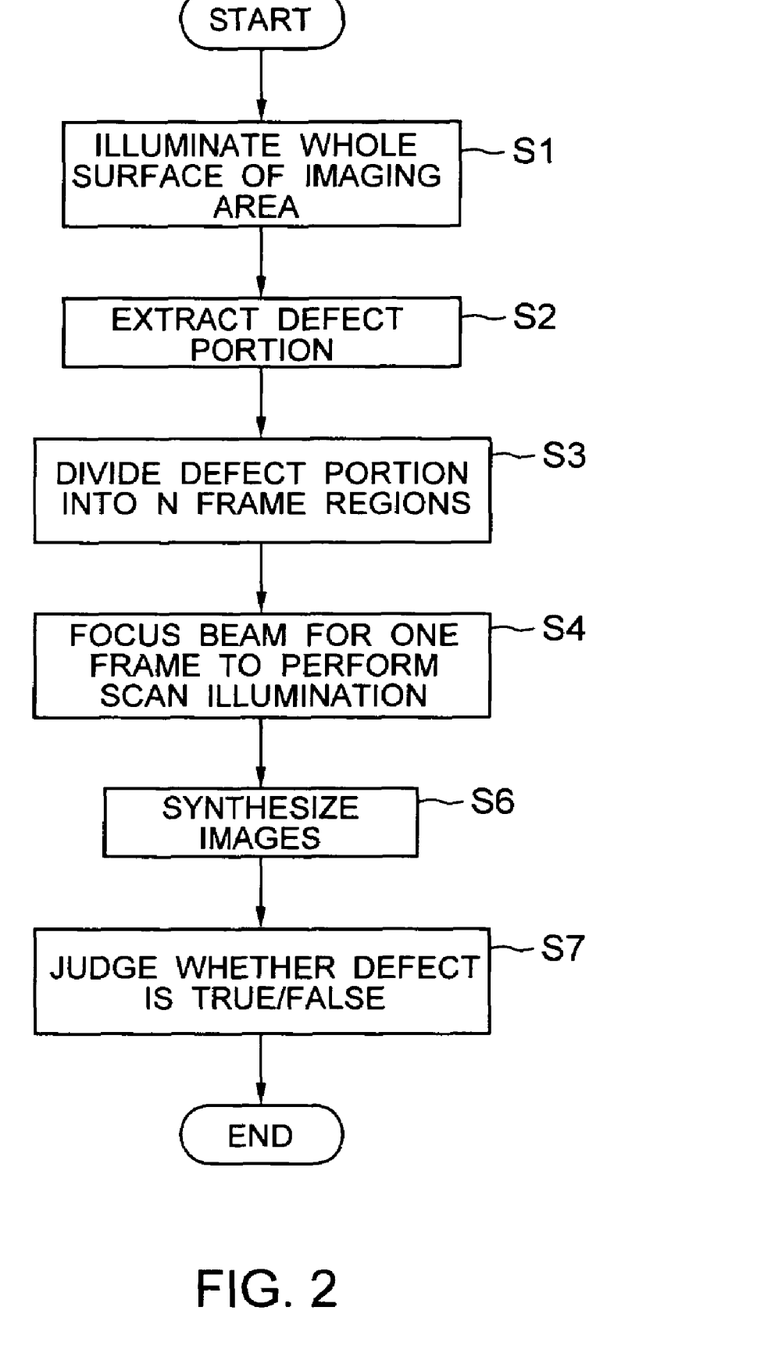
FIG. 2 is a flowchart showing a schematic procedure of one example of a defect inspection method using a defect inspection apparatus shown in FIG. 1.

FIG. 2 is a flowchart showing a schematic procedure of a defect inspection method according to the present embodiment, and FIGS. 3A to 5 are explanatory views of the defect inspection method shown in FIG. 2.

Figure 3A:
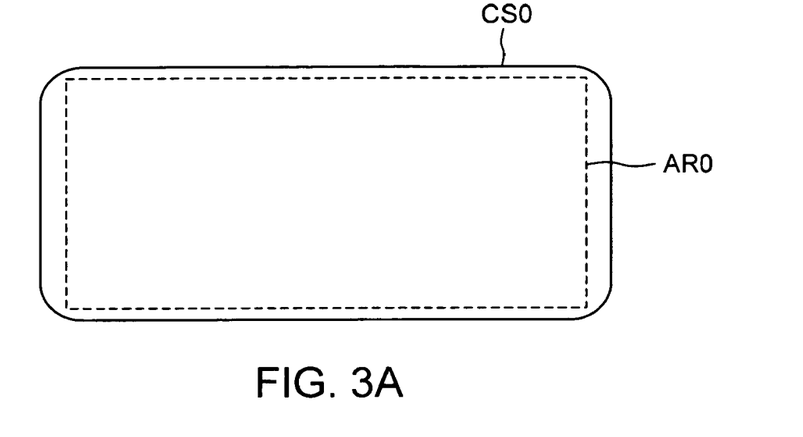
FIGS. 3A to 3C are explanatory views of a defect inspection method shown in FIG. 2.
Figure 3B:
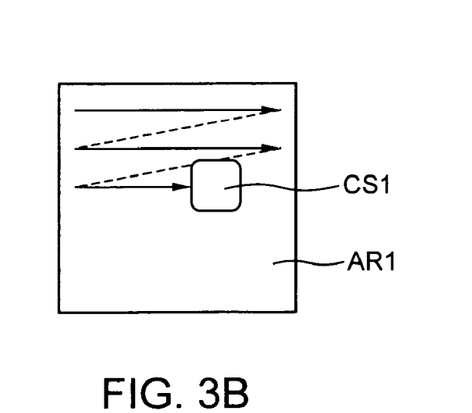

First, as shown in FIG. 3A, while a whole surface of an imaging area AR0 is illuminated with an illuminative beam CS0, a whole inspection area is imaged by stage-scanning by the stage 40 (FIG. 2, step S1), and a defect portion is extracted (step S2). Next, the extracted defect portion is equally divided into N regions (hereinafter referred to as frame regions) (step S3), and a beam diameter is limited to a size for one frame. As shown in FIG. 3B, an imaging area AR1 which is a defect portion is scanned/illuminated with a focused illuminative beam CS1 (step S4). To reduce the beam diameter by the defect inspection apparatus shown in FIG. 1, the control signal may be supplied from the controller 64 to adjust the quadrupole lens 18. The defect portion of the illuminative beam is scanned/illuminated by the primary beam deflector 22. At a time when inspection is executed by collective illumination, while the stage 40 is continuously moved, the image is picked up by the TDI sensor. At a review time, while the stage 40 is allowed to stand still, the imaging is performed using the STILL mode of the TDI sensor. Accordingly, the image can be acquired by the frame unit.

Figure 4A:
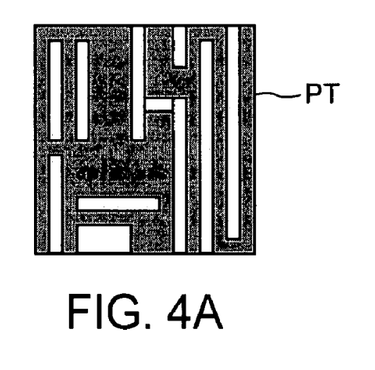
FIGS. 4A and 4B are explanatory views of the defect inspection method shown in FIG. 2.
Figure 4B:
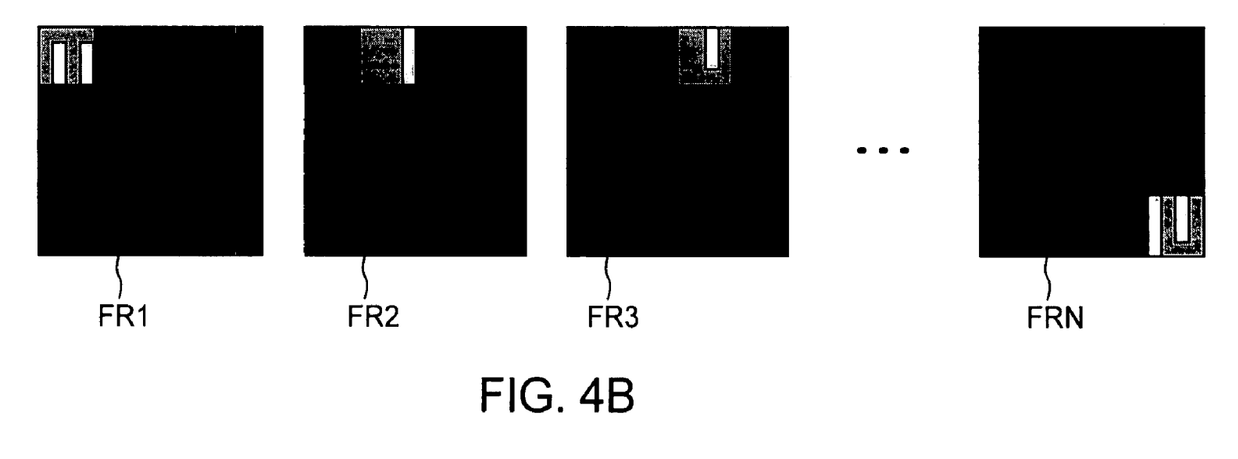
Figure 5:
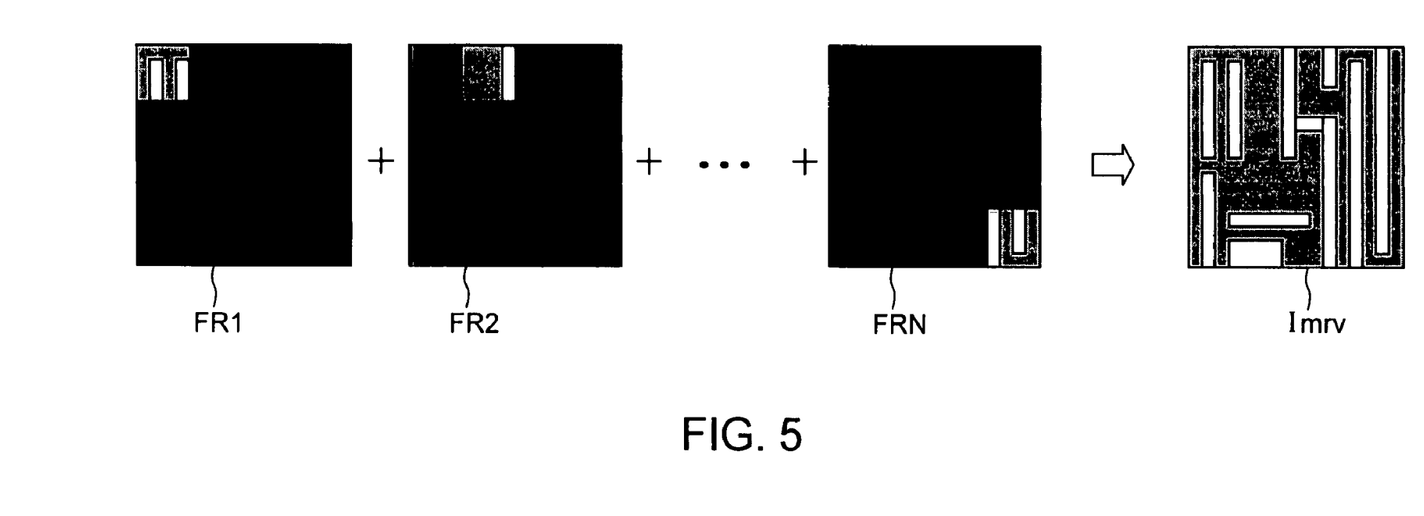
FIG. 5 is an explanatory view of the defect inspection method shown in FIG. 2.
Figure 6A:
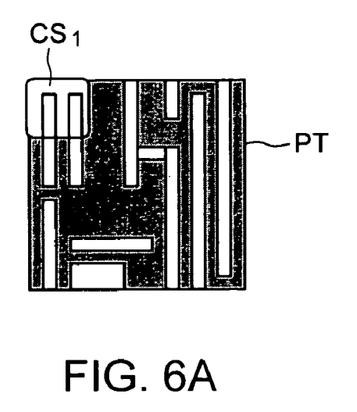
FIGS. 6A and 6B are schematic diagrams showing an influence of a noise electron in a case where a review image is obtained by an addition process.
Figure 6B:
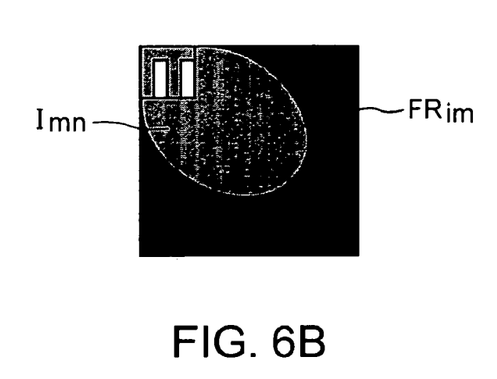

FIGS. 4A and 4B schematically show a state in which a frame image is continuously picked up in the STILL mode of the TDI sensor by scan illumination. When an imaging target pattern PT shown in FIG. 4A is continuously scanned/illuminated with the beam, frame images FR1 to FRN shown in FIG. 4B can be obtained. It is to be noted that the scan illumination is repeated many times, not once, in the same manner as in a general SEM apparatus, and thereafter an integration process is performed. Consequently, an S/N of the reviewed image can be enhanced.

Next, the process returns to FIG. 2, and the obtained images of the imaging frames FR1 to FRN are synthesized by image processing (step S6). Accordingly, as shown in a schematic diagram of FIG. 5, a synthesized image (review image) Imrv can be obtained in accordance with the imaging target pattern PT. The image processing is executed, when the image processor 78 adds image data of the imaging frames FR1 to FRN in the defect inspection apparatus shown in FIG. 1.

Finally, it is judged using the obtained review image Imrv whether a defect extracted by the collective illumination is true/false (step S7). This judgment is executed by the host computer 80 of the defect inspection apparatus shown in FIG. 1.

Figure 3C:
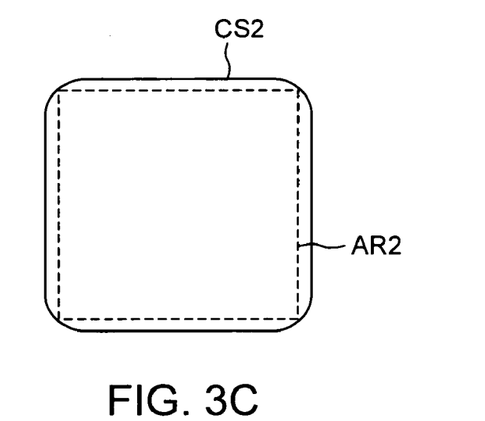

Even at a review time, a whole imaging area AR2 of the extracted defect portion can be imaged by the collective illumination in the same manner as in an inspection time, for example, as in an illuminative beam CS2 shown in FIG. 3C. However, the scan illumination is superior to the collective illumination in that an influence of a space charge effect can be suppressed, and therefore a high-resolution image can be obtained. In general, the scan illumination has a demerit that an imaging time is required as compared with the collective illumination, but a high speed is not required at the review time unlike the inspection time, and therefore this demerit does not raise any problem.

Thus, according to the present embodiment, a high-resolution review image can be obtained.

SECOND EMBODIMENT

Next, a second embodiment of the present invention will be described with reference to FIGS. 6A to 10C. A defect inspection method according to the present embodiment can be executed using the defect inspection apparatus shown in FIG. 1.

In the first embodiment, frame images obtained by scan illumination are simply added to acquire a review image. However, as in a region denoted with symbol Imn in an imaging frame FRim of FIG. 6B obtained by the scan illumination with respect to an imaging target pattern PT of FIG. 6A, the frame image sometimes include a noise image by an noise electron which does not contribute to image formation. In this case, when the respective frame images are added as such, a review image inferior in S/N is obtained. In the present embodiment, there is provided a method in which a mask image is prepared, a masking process is executed prior to an addition process, and accordingly the S/N of the review image is enhanced.

Figure 7:
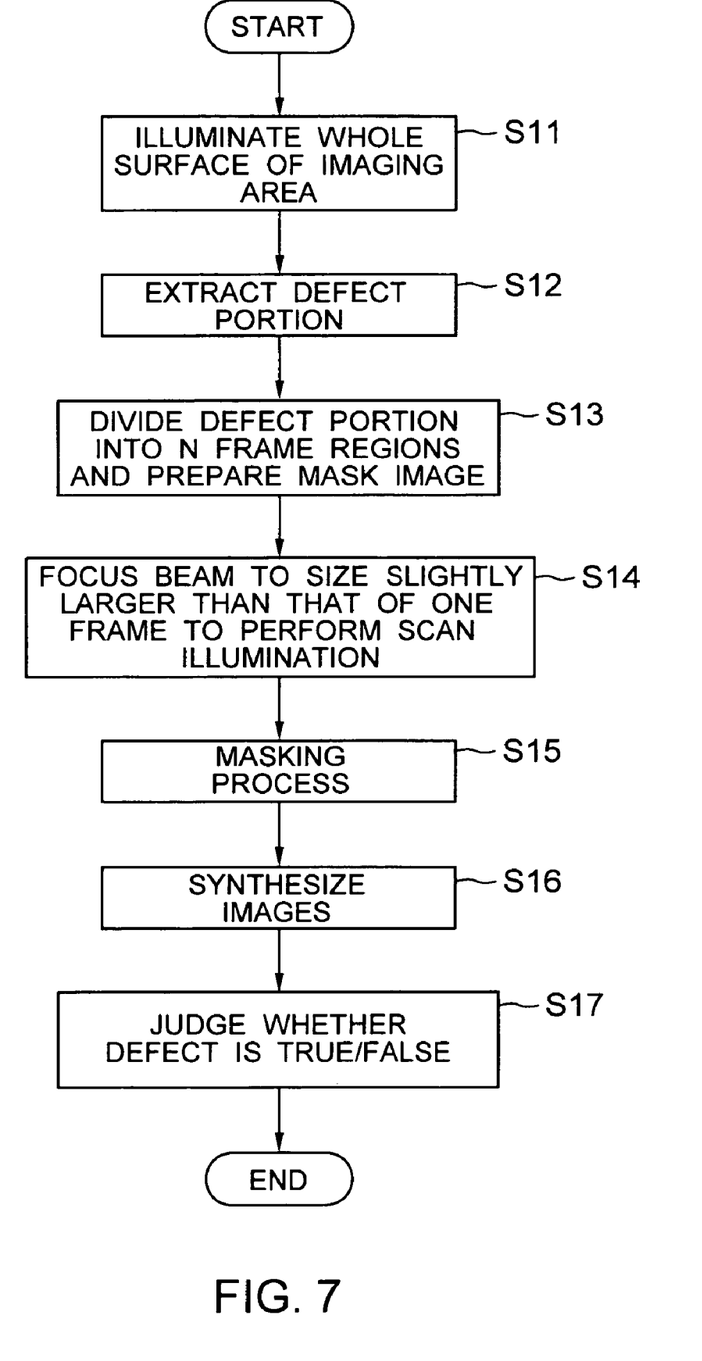
FIG. 7 is a flowchart showing a schematic procedure of another example of the defect inspection method using the defect inspection apparatus shown in FIG. 1.

FIG. 7 is a flowchart showing a schematic procedure of a defect inspection method of the present embodiment.

First, in the same manner as in an inspection method according to a conventional art, while a whole surface of an imaging area AR0 is illuminated with an illuminative beam CS0, a whole inspection area is imaged by stage-scanning by a stage 40 (step S11), and a defect portion is extracted (step S12). Next, the extracted defect portion is divided into N frame regions FR1 to FRN, and a mask image is prepared in which a window is opened in an illumination region in accordance with each frame region (step S13). Subsequently, the corresponding frame image and the mask image are subjected to a masking process, that is, a logical product is taken. Accordingly, an image from which any influence of noise has been removed is prepared (step S15). Thereafter, in the same manner as in the first embodiment, N images subjected to the masking process are synthesized to acquire a review image (step S16), and it is judged using the obtained review image whether the defect extracted by collective illumination is true/false using an obtained review image (step S17).

Figure 8A:
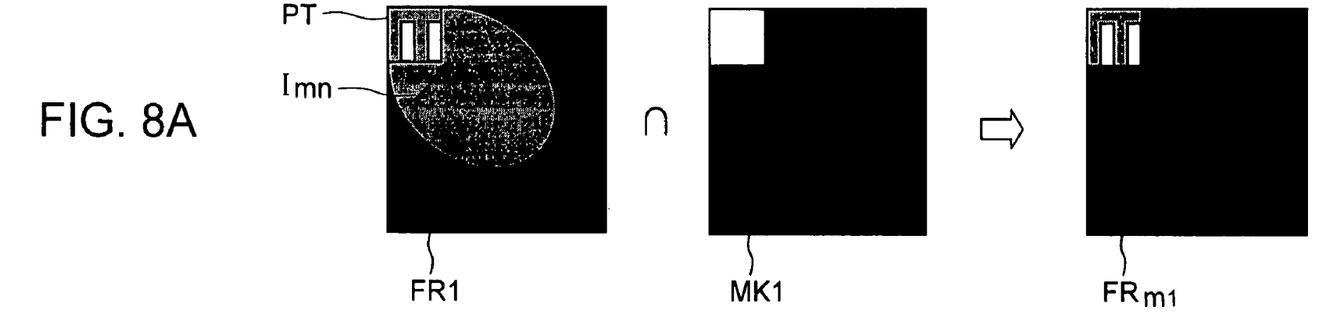
FIGS. 8A and 8B are explanatory views of the defect inspection method shown in FIG. 7.
Figure 8B:
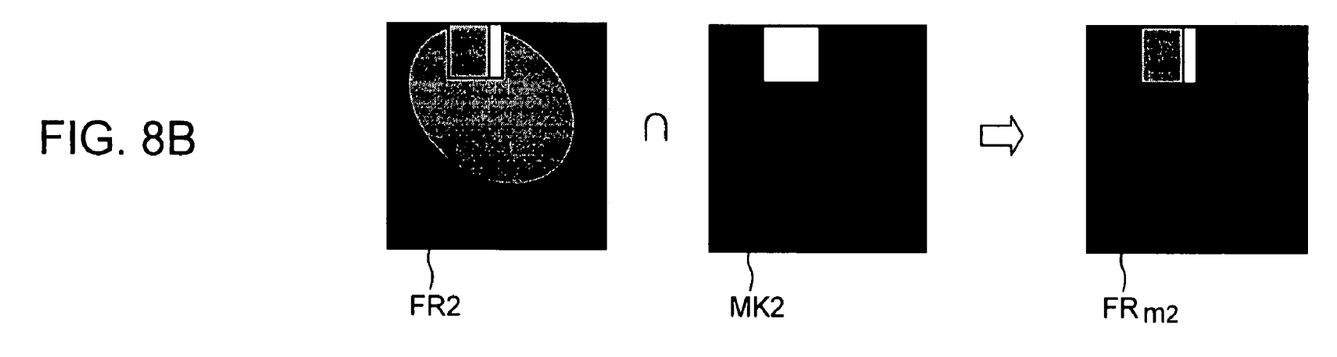

A specific example of the masking process will be described with reference to schematic diagrams of FIGS. 8A and 8B. FIG. 8A shows a state in which a logical product is taken between a frame image FR1 obtained by first beam illumination in continuous scanning from a corner of an imaging target pattern PT, the corner being a start point, and a mask MK1 prepared beforehand corresponding to the frame image FR1 to remove a noise image Imn, and an image FRm1 subjected to the masking process is obtained. FIG. 8B shows a state in which a logical product is taken between a frame image FR2 obtained by second beam illumination following the frame image FR1, and a mask MK2 prepared beforehand corresponding to the frame image FR2 to obtain an image FRm2 subjected to the masking process.

Figure 9A:
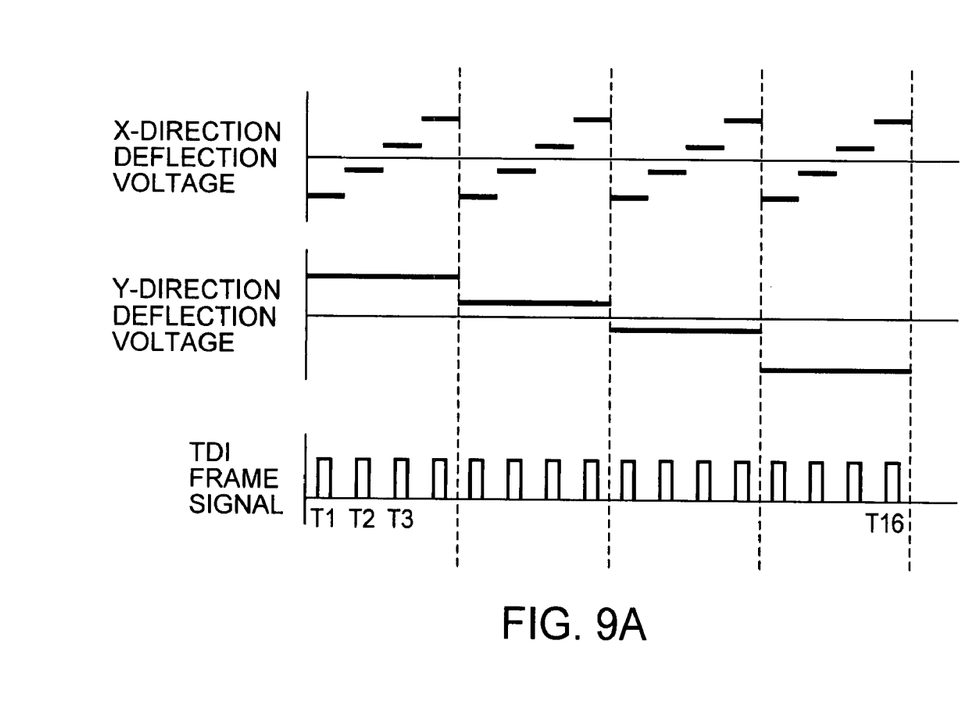
FIGS. 9A to 9C are explanatory views of the defect inspection method shown in FIG. 7.
Figure 9B:
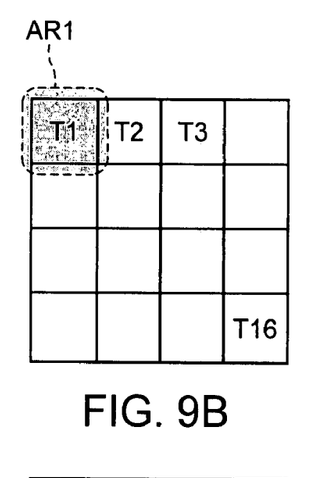
Figure 9C:
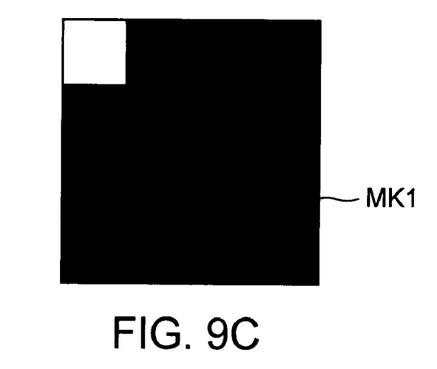
Figure 10A:
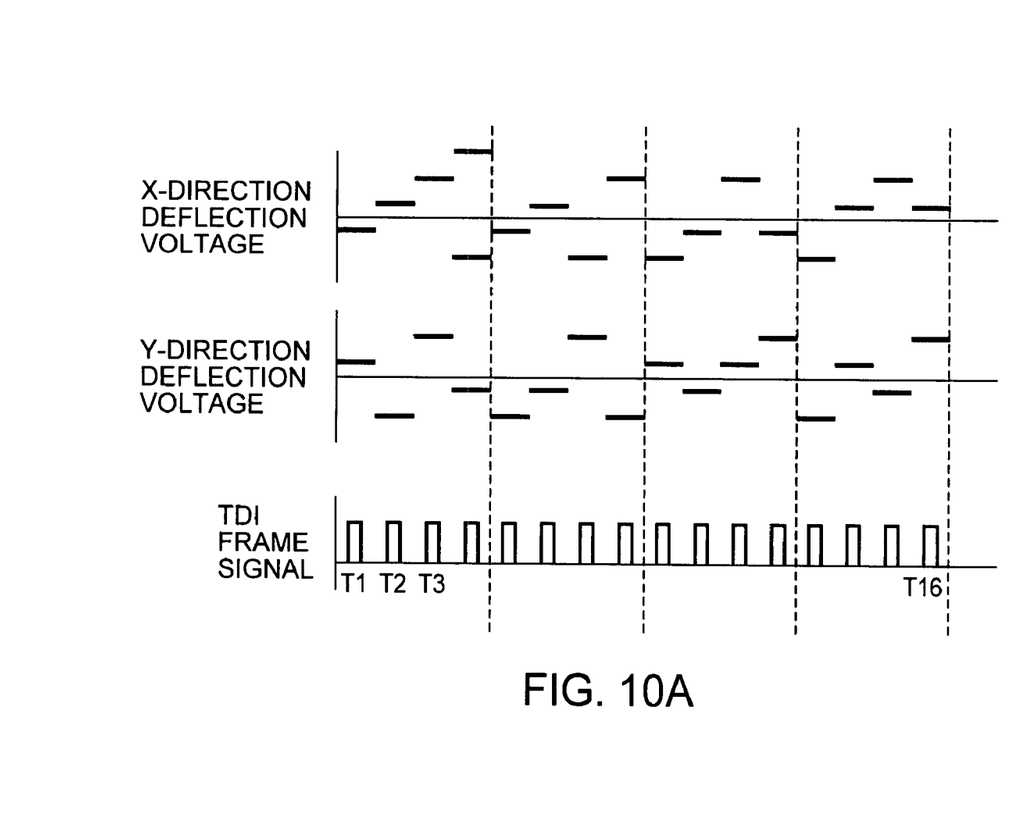
FIGS. 10A to 10C are explanatory views of the defect inspection method shown in FIG. 7.
Figure 10B:
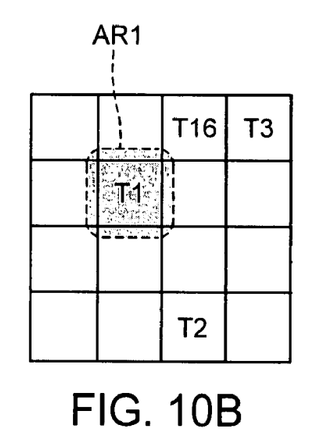
Figure 10C:
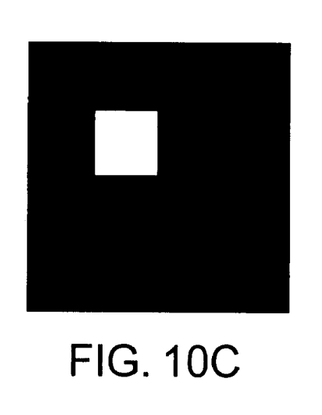

FIGS. 9A to 9C are explanatory views showing a relation among a deflection voltage for a primary beam deflector, a frame signal of a TDI sensor, and a mask image. FIG. 9A shows a relation between a deflection voltage (X-direction and Y-direction) applied to a primary beam deflector 22 of the defect inspection apparatus shown in FIG. 1, and frame signals T1 to T16 applied to a TDI sensor 76. FIG. 9B shows a relation between a position of a continuously scanned illumination area AR1, and the frame signals T1 to T16. Furthermore, FIG. 9C shows a mask image MK1 at a time when a frame signal T1 is applied. As shown in FIG. 9A, the deflection voltage is generated in a step manner in synchronization with the frame signals T1 to T16 to the TDI sensor 76. As apparent from comparison of FIG. 9A with FIG. 9B, in the present embodiment, an unmask region (window portion) of a mask image has a size obtained by dividing the imaging area into 4×4 regions, but the size of the illumination area AR1 is set in such a manner as to be slightly larger than that of the unmask region. Consequently, uniformity of the image can be prevented from being influenced in a boundary of beam application. In an example shown in FIGS. 9A to 9C, a deflection voltage is generated in such a manner that the illumination area continuously moves in order from a left upper corner of the imaging area, but the present invention is not limited to this example. As in an example shown in FIGS. 10A to 10C, the deflection voltage may be generated in such a manner that the illumination area AR1 moves in an irregular order by random scanning.

As described above, according to the present embodiment, a review image further superior in resolution and S/N can be obtained.

(3) Program

A series of procedure of the above-described defect inspection method may be incorporated in a program, and read and executed as a recipe file in a computer of an SEM apparatus. Accordingly, the above-described defect inspection method can be realized using a general-purpose SEM apparatus including the computer capable of processing the image. A series of procedure of the above-described defect inspection method may be stored as a program to be executed by the computer of the SEM apparatus in recording mediums such as a flexible disk and CD-ROM, and read and executed in the computer of the SEM apparatus.

The recording mediums are not limited to portable mediums such as a magnetic disk and an optical disk, and may be fixed recording mediums such as a hard disk drive and a memory. A program in which a series of procedure of the defect inspection method is incorporated may be distributed via a communication circuit (including radio communication) such as internet. Furthermore, the series of procedure of the defect inspection method may be encrypted, modulated, or compressed. In this state, the method may be distributed via a wire circuit such as internet or a radio circuit. The method may be stored in the recording medium, and distributed.

(4) Manufacturing Method of Semiconductor Device

A semiconductor device is manufactured using the above-described defect inspection method, and it is accordingly possible to manufacture a semiconductor device with a high throughput and yield.

As described above, several modes for carrying out the present invention have been described, but the present invention is not limited to the above-described modes, and can be variously modified and applied within the scope thereof. For example, in the above-described embodiments, the imaging area has been divided into 4×4 regions, but the number of divisions is not limited to this, and an arbitrary number can be set in accordance with precision. In the above-described embodiment, a case where an electron beam is used as a charged particle beam has been described, but the present invention is not limited to this case, and is applicable even to a defect inspection apparatus, for example, using ion beams.

What is claimed is:

1. A defect inspection apparatus comprising:
a charged particle beam source which emits a charged particle beam to illuminate the charged particle beam onto a sample as a primary beam, the sample generating a secondary charged particle, a reflective charged particle, and/or a back-scattered charged particle from the surface thereof by the illumination of the primary beam;
an image pickup which includes an imaging element having a light receiving face receiving at least one of the secondary charged particle, the reflective charged particle, and the back-scattered charged particle generated from the sample and which outputs a signal indicating a state of the surface of the sample;
a mapping projection system which maps/projects at least one of the secondary charged particle, the reflective charged particle, and the back-scattered charged particle as a secondary beam and which makes the beam to form an image on the light receiving face of the imaging element;
a controller which adjusts a beam diameter of the primary beam in such a manner as to apply the beam to the sample with a size smaller than that of an imaging region as a target of review to scan the imaging region and which allows the image pickup to pick up a plurality of frame images;
an image processor which processes the plurality of obtained frame images to prepare a review image; and
a defect judgment unit which judges a defect of the sample based on the review image.

2. The defect inspection apparatus according to claim 1, wherein the image processor prepares a plurality of mask images each having a non-mask region in accordance with the respective frame images beforehand, and
the review image is prepared by synthesizing a plurality of images obtained by taking each logical product of the mutually corresponding frame images and the mask images.

3. The defect inspection apparatus according to claim 2, wherein the beam diameter of the primary beam is adjusted in such a manner that the primary beam is illuminated onto the sample with a size larger than that of the non-mask region.

4. The defect inspection apparatus according to claim 1, wherein the controller generates a stepped scanning signal, and supplies the signal to the charged particle beam source in such a manner that the imaging region is scanned with the primary beam in synchronization with a frame rate of the imaging element.

5. The defect inspection apparatus according to claim 4, wherein the stepped scanning signal is generated in such a manner that the imaging region is scanned in an irregular order by the primary beam.

* * * * *